United States Patent
Fujisaki et al.

(10) Patent No.: US 10,945,754 B2
(45) Date of Patent: Mar. 16, 2021

(54) ULTRASOUND DEVICE

(71) Applicant: OLYMPUS CORPORATION, Hachioji (JP)

(72) Inventors: Ken Fujisaki, Sagamihara (JP); Takamitsu Sakamoto, Hachioji (JP); Michio Takayama, Taito-Ku (JP); Hideto Yoshimine, Hachioji (JP); Ken Yokoyama, Fussa (JP); Ryo Miyasaka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 180 days.

(21) Appl. No.: 16/396,261

(22) Filed: Apr. 26, 2019

(65) Prior Publication Data
US 2019/0247058 A1 Aug. 15, 2019

Related U.S. Application Data

(63) Continuation of application No. PCT/JP2016/082184, filed on Oct. 28, 2016.

(51) Int. Cl.
*A61B 17/16* (2006.01)
*A61B 17/32* (2006.01)

(52) U.S. Cl.
CPC ...... *A61B 17/320068* (2013.01); *A61B 17/16* (2013.01); *A61B 17/1631* (2013.01);
(Continued)

(58) Field of Classification Search
CPC .... A61B 17/1631; A61B 2017/320073; A61B 17/320068
See application file for complete search history.

(56) References Cited

U.S. PATENT DOCUMENTS

| 5,188,102 A | * | 2/1993 | Idemoto | A61B 17/320068 604/22 |
| 5,205,807 A | * | 4/1993 | Adams, Jr. | B29C 37/0021 493/125 |

(Continued)

FOREIGN PATENT DOCUMENTS

| EP | 2 119 403 A1 | 11/2009 |
| JP | H0274014 U | 6/1990 |

(Continued)

OTHER PUBLICATIONS

Jan. 10, 2017 International Search Report issued in International Application No. PCT/JP2016/082184.

*Primary Examiner* — Christian A Sevilla
(74) *Attorney, Agent, or Firm* — Oliff PLC

(57) ABSTRACT

An ultrasound device includes: an ultrasound generator; an ultrasound probe; and a distal end treatment portion capable of forming a bone hole when pressed against a bone. The distal end treatment portion includes a base portion, and a distal end portion. The distal end portion includes projections and a valley portion between adjacent projections. Each projection is formed of at least one excision surface that is inclined from a base of the projection to a distal top of the projection. The excision surface is capable of finely crushing the bone. The valley portion includes a valley peak at a distal-most meeting point of adjacent projections such that a surface of the valley extending distally from a point at which the valley meets an outer surface of the base portion to the valley peak is inclined.

19 Claims, 7 Drawing Sheets

(52) U.S. Cl.
CPC ............ *A61B 2017/320073* (2017.08); *A61B 2217/007* (2013.01)

(56) References Cited

U.S. PATENT DOCUMENTS

| | | | |
|---|---|---|---|
| 8,057,498 B2 * | 11/2011 | Robertson | A61B 17/320068 606/169 |
| 2006/0004396 A1 | 1/2006 | Easley et al. | |
| 2006/0122543 A1 | 6/2006 | Mayer et al. | |
| 2006/0253050 A1 | 11/2006 | Yoshimine et al. | |
| 2010/0167235 A1 | 7/2010 | Vercellotti et al. | |

FOREIGN PATENT DOCUMENTS

| | | |
|---|---|---|
| JP | 2005-152098 A | 6/2005 |
| JP | 2007-500521 A | 1/2007 |
| JP | 2010-504138 A | 2/2010 |
| WO | 2006/030563 A1 | 3/2006 |

\* cited by examiner

DISTAL END SIDE
↕
PROXIMAL END SIDE

ULTRASOUND DEVICE

This application is a continuation of International Application No. PCT/JP2016/082184, filed on Oct. 28, 2016, the entire contents of which are incorporated herein by reference.

BACKGROUND

The present disclosure relates to an ultrasound device.

In general, as a surgical operation including treatment for forming a bone hole in a bone in a case of, for example, joint surgery, there is anterior cruciate ligament reconstruction surgery for compensating an injured ligament for a new ligament. This anterior cruciate ligament reconstruction surgery includes treatment for forming a bone hole in a bone at a fixed position for transplanting the new ligament. With currently used manipulation, a circular bone hole in cross section is formed by using an instrument having a rotary blade, such as a drill, and by moving forward the rotating drill blade.

At an end portion of the ligament to be transplanted, in a case of an STG method, semitendinosus tendons or gracilis muscles are folded in an overlaid manner, whereas, in a case of a BTB method, a bone chip is cut out into a square to which a patellar tendon is connected; therefore, in both methods, each of the cross sections thereof is not circular. For example, the cross-sectional shape thereof is sometimes a rectangular shape.

Thus, if a part to be inserted into a bone hole is different from the cross-sectional shape of the formed bone hole, a round shaped bone hole is to be formed such that the insertion part is inserted and a gap is accordingly generated around the part. As a method for coping with this problem, it is possible to shape the cross section of the bone hole from a circular bone hole into a rectangular shape by using an instrument, such as a rectangular block shaped dilator; however, because the hole is formed by pushing and broadening a relatively soft cancellous bone, the shape of the finished hole is not a desired shape. There may be a case in which this method is not able to be used depending on a bone state of a patient and, furthermore, an operation is performed in a narrow area that is used for treatment; therefore, this is not an easy operation.

Furthermore, for example, there has been proposed an ultrasound handpiece that applies ultrasound vibrations that mainly vibrate back and forth (axial direction) to a probe having a chip or a head capable of forming a bone hole and that forms a hole having a shape associated with the cross-sectional shape of the distal end of the probe. When scraping off a bone by using ultrasound vibrations, the distal end surface of the vibrating probe is pressed against the bone and mechanically comes into collision (hammering effect), thereby the bone is crushed into fine granularities.

The distal end of the probe has substantially a cylindrical shape and is provided with a plurality of cutting elements sharply protruding at equal intervals around the circumference of the probe. These cutting elements are inclined such that the inclination of inclined surfaces on the inner side are inclined toward the center and, at the center thereof, an outlet head for flowing out a fluid, such as a physiological saline solution is provided. The configuration thereof is such that the fluid flowing out from the outlet head flows out, while swallowing cutting debris, from groove-shaped fluid channels that are provided between each of the cutting elements and that spread radially; flow, on the side face of the probe along the fluid channels thereof, from the distal end side toward the proximal end side; and is discharged from the rear side of the probe.

SUMMARY

There is a need for an ultrasound device that is capable of forming a bone hole having a flat wall surface whose shape and size are matched with those of a part to be fixed at the time of treatment and that has a high processing speed by discharging, from the excision surface, cutting debris generated when the bone hole is formed and preventing the cutting debris from being retained.

An ultrasound device according to one aspect of the present disclosure includes: an ultrasound generator capable of generating ultrasound vibrations; and an ultrasound probe that is acoustically connected to the ultrasound generator at a proximal end side of the ultrasound probe and that transmits the ultrasound vibrations to a distal end side of the ultrasound probe. A distal end treatment portion is provided on the distal end side of the ultrasound probe and is designed to form a bone hole when pressed against a bone. The distal end treatment portion includes a base portion that forms the same cross section as the cross section of the bone hole, and a distal end portion that is formed on a distal end side of the base portion. The distal end portion includes a plurality of projections arranged in a row, and a valley that is formed between the projections. Each projection is formed of at least one excision surface that is inclined from a base of the projection to a distal top of the projection. The excision surface is designed to finely crush the bone. The valley adjoins adjacent projections. The valley includes a valley peak at a distal-most meeting point of the adjacent projections such that a surface of the valley extending distally from a point at which the valley meets an outer surface of the base portion to the valley peak is inclined.

The above and other features, advantages and technical and industrial significance of this disclosure will be better understood by reading the following detailed description of presently preferred embodiments of the disclosure, when considered in connection with the accompanying drawings.

DETAILED DESCRIPTION

In the following, preferred embodiments of an ultrasound probe of an ultrasound device will be explained with reference to accompanying drawings.

Figure 1:
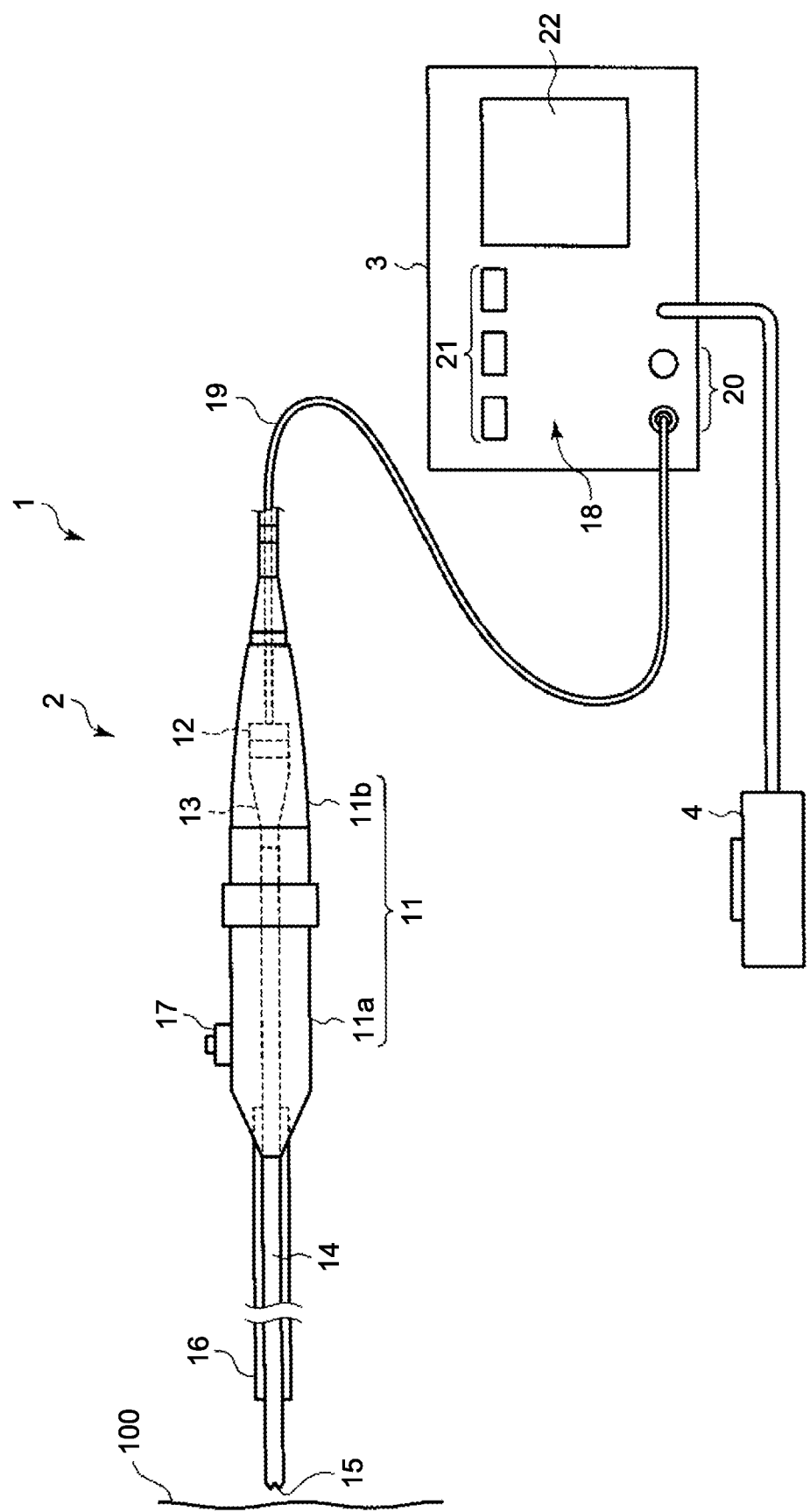
FIG. 1 is a diagram illustrating a system configuration of an ultrasound device according to an exemplary embodiment.

FIG. 1 is a diagram illustrating a system configuration of an ultrasound device according to an exemplary embodiment.

An ultrasound device system 1 according to the embodiment is constituted by mainly using an ultrasound device 2, a power supply unit 3, and a foot switch 4 that instructs on/off of an ultrasound vibration. The ultrasound device 2 and the power supply unit 3 are connected by a cable 19, in which a supply of electrical power to be driven or communication of a control signal is performed. The power supply unit 3 is provided with, on a front surface 18, a plurality of connectors 20 for connecting the cable 19, various kinds of operation switches 21, and a display screen 22 for displaying information needed for treatment. Furthermore, the power supply unit 3 is separately used in combination with an endoscope system in accordance with manipulation or surgical contents.

The ultrasound device 2 is constituted by a device main body 11 and an ultrasound probe 14. The device main body 11 is constituted by a housing 11a that has a tube shape and through which the ultrasound probe 14 passes and an ultrasound transducer unit (ultrasound generating unit) 11b that is capable of being attached to and removed from the housing 11a. The ultrasound transducer unit 11b accommodates therein an ultrasound vibration element (ultrasound generating unit) 12 formed of a piezoelectric element or the like and a horn 13 that efficiently transmits ultrasound. In a state in which the ultrasound transducer unit 11b is attached to the housing 11a, the proximal end side of the ultrasound probe 14 and the distal end side of the horn 13 are acoustically connected and the ultrasound vibration generated in the ultrasound vibration element 12 is transmitted to a distal end treatment portion 15, which will be described later, of the ultrasound probe 14. On the upper surface of the housing 11a, an operation switch 17 that instructs on/off of the ultrasound vibration by using a finger operation. The foot switch 4 has the same function as that of the operation switch 17. Furthermore, the ultrasound probe 14 is covered by a sheath 16 up to the point having an arbitrary length starting from the housing 11a.

The ultrasound device system 1 configured in this way presses, against a bone, the distal end treatment portion 15 that is included in the ultrasound device 2 and in which the ultrasound vibration is applied; applies a hammering action; and crushes the bone into fine granularities. Furthermore, the ultrasound device 2 according to the embodiment is configured such that a mechanism of supplying and draining a perfusion fluid is not provided; however, it is also possible to provide the mechanism of supplying and draining a perfusion fluid in accordance with a use application. Furthermore, it may also be possible to use the ultrasound device 2 together with an endoscope that has the mechanism of supplying and draining the perfusion fluid.

Figure 2:
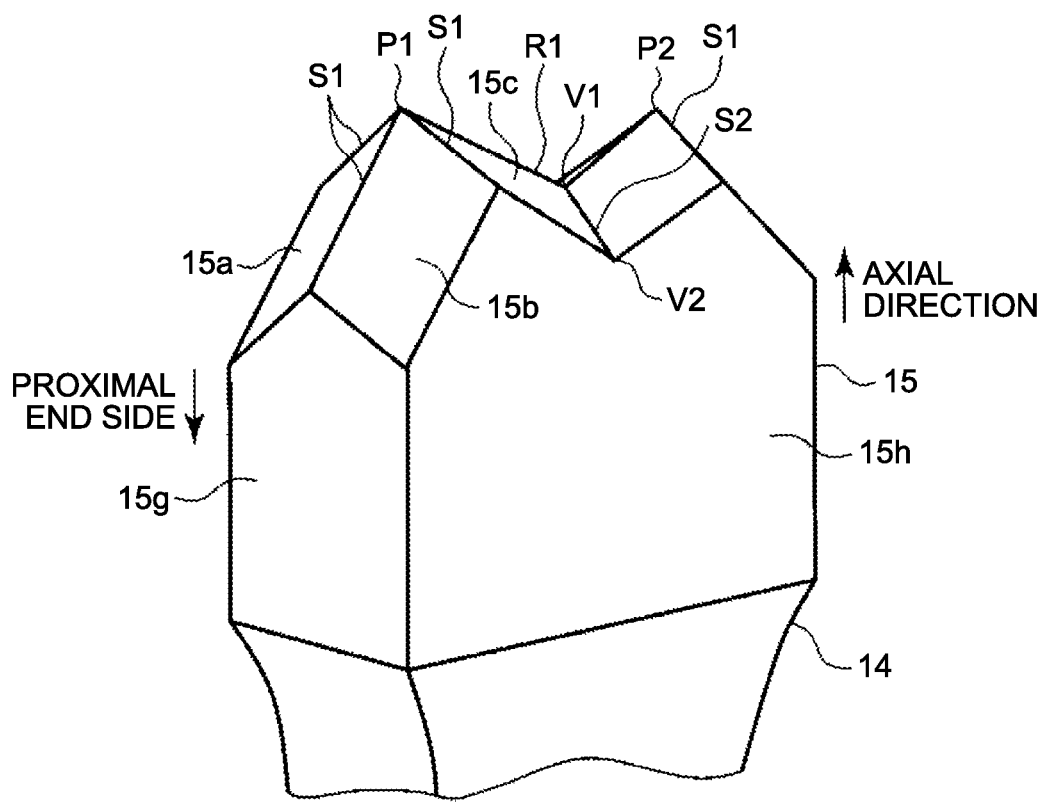
FIG. 2 is a diagram illustrating an appearance shape, viewed from the oblique direction, of a distal end treatment portion of the ultrasound device according to an exemplary embodiment.
Figure 3:
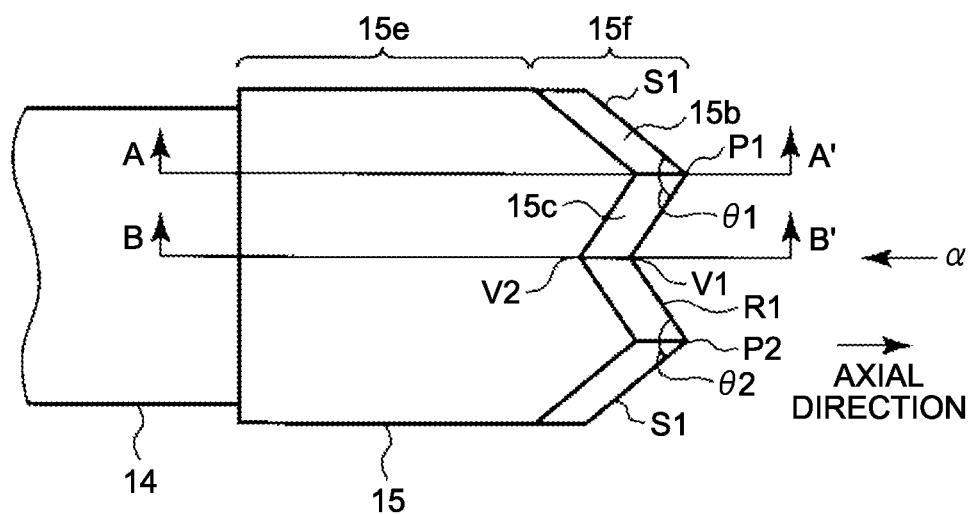
FIG. 3 is a diagram illustrating an appearance shape, viewed from the side direction, of a distal end treatment portion of the ultrasound device.
Figure 4:
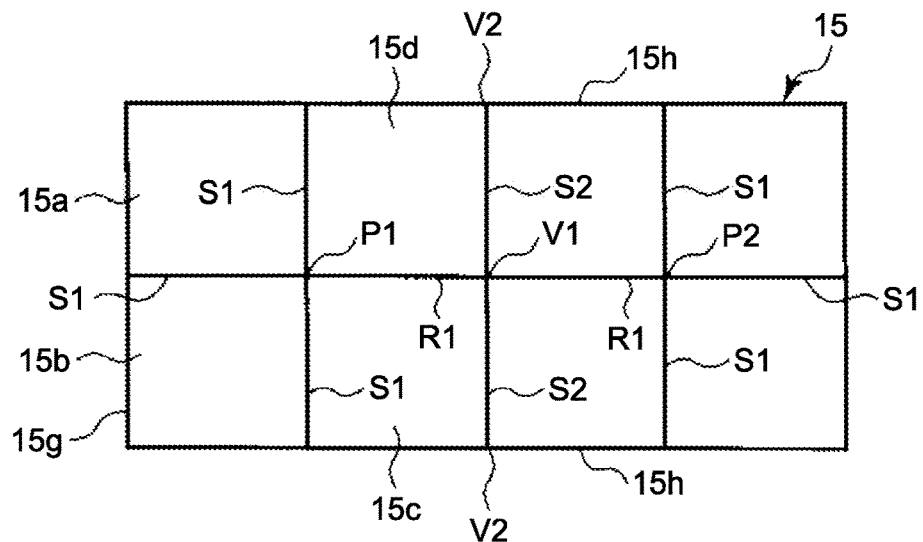
FIG. 4 is a diagram illustrating an appearance shape, viewed from the direction longitudinal axis, of a distal end of the distal end treatment portion of the ultrasound device.
Figure 5:
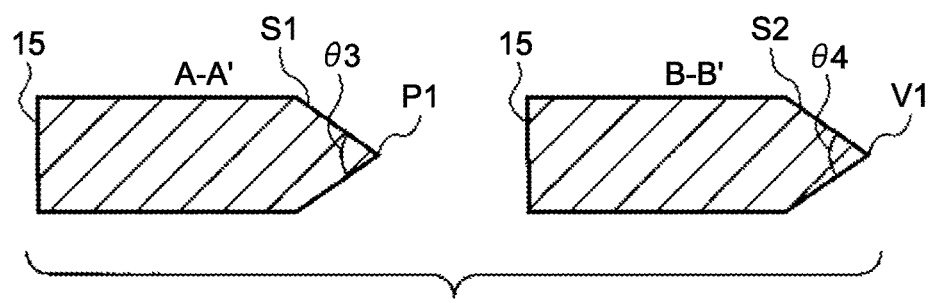
FIG. 5 is a diagram illustrating a cross-sectional shape of the distal end treatment portion illustrated in FIG. 2.
Figure 6:
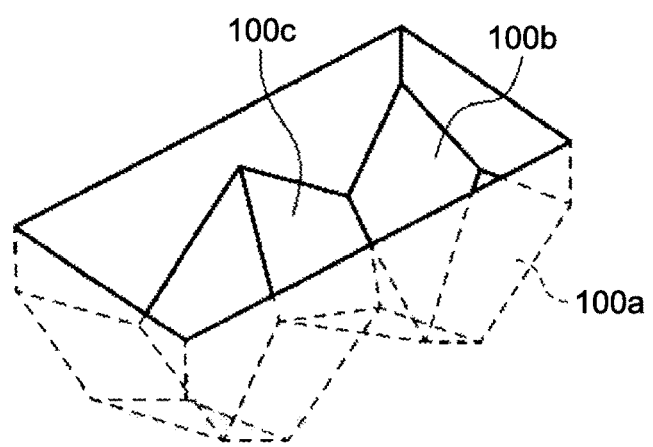
FIG. 6 is a diagram illustrating a shape of a bottom portion of a bone hole formed by the ultrasound device.

In the following, a distal end treatment portion provided at the distal end of the ultrasound probe according to the present embodiment will be described with reference to FIG. 2 to FIG. 7. Here, FIG. 2 is a diagram illustrating an appearance shape, viewed from the oblique direction, of a distal end treatment portion of the ultrasound device according to the present embodiment. FIG. 3 is a diagram illustrating an appearance shape, viewed from the side direction, of a distal end treatment portion; FIG. 4 is a diagram illustrating a projected shape (appearance shape) of the distal end of the distal end treatment portion viewed from the direction of the longitudinal axis (hereinafter, referred to an axial direction); and FIG. 5 is a diagram illustrating a cross-sectional shape of the distal end treatment portion illustrated in FIG. 2. FIG. 6 is a diagram illustrating a shape of a bottom portion of a bone hole formed by the ultrasound device.

The ultrasound probe 14 according to the embodiment is formed integrally with the distal end treatment portion 15 by using, for example, a titanium alloy, or the like. The distal end treatment portion 15 is an excision tool that uses ultrasound vibrations and is constituted by, as illustrated in FIG. 3, a base portion 15e and a distal end portion 15f. In a description below, in the axial direction (longitudinal axis) of the direction in which the ultrasound probe 14 extends, the side closer to the housing 11a is referred to as a proximal end side and the side that is the extending direction of the axial direction is referred to as a distal end side.

The base portion 15e is located on a proximal end side of the distal end treatment portion 15 (i.e., on a side closer to the housing 11a) and is the maximum external shape portion that defines a contour shape (or an external shape) of a hole to be formed. This is because, a bone hole having a shape and a size of the maximum external shape portion is to be formed and a shape and a size of the bone hole to be formed are changed in accordance with a change in the maximum external shape portion. The shape of the maximum external shape portion according to the embodiment is, as an example, rectangular as illustrated in FIG. 4 viewed from the direction of a illustrated in FIG. 3. This rectangular shape (rectangular) is used as an example of coping with the anterior cruciate ligament reconstruction surgery described above and the shape is not limited to the rectangular shape. By forming the cross-sectional shape of the base portion 15e, such as an elliptical shape or a polygonal shape other than the rectangular shape in accordance with a use application, it is possible to form various kinds of desired holes.

The distal end portion 15f is a distal end portion that is continuously provided on the base portion 15e and is closer to the base portion 15e than the housing 11a. Here, the distal end side is referred to as the region ahead of the area in which a slope is started after being curved from the probe main body with respect to the axial direction. The distal end portion 15f according to the embodiment is connected to an edge line R1, which connects a top portion P1, a valley portion V1, and a top portion P2; is connected to a ridge line S1; and is provided with two double-edged excision portions that are formed in a mountain shape on an inclined surface having a downward slope on the proximal end side. At this time, the ridge line S1 diagonally descend from the top portions P1 and P2 toward the proximal end side.

Specifically, in FIG. 2 and FIG. 4, projection lines that are arranged in a row at the center of the distal end surface and that are starting from the top portions P1 and P2 toward front/back faces (outer surfaces) 15h and both side faces (outer surfaces) 15g are referred to as ridge lines S1 and a depression line starting from the valley portion V1 toward the valley portion V2 of the front/back faces 15h is referred to as a valley line S2. Furthermore, the line that connects the top portion P1 to the top portion P2 via the valley portion V1 is referred to as an edge line R1. Furthermore, in the embodiment, the ridge line S1 descends in the direction in which the edge line R1 is extended and in the direction orthogonal to the edge line R1 so as to move toward the proximal end side and then reaches the outer surfaces 15h and 15g.

In the embodiment, the distal end portion 15f includes, as illustrated in FIG. 4, the two top portions P1 and P2 that protrude at equal intervals that are obtained by dividing the longer side of the distal end surface viewed from the α direction into two. As illustrated in FIG. 2, excision surfaces 15a and 15b, which are formed of inclined surfaces that start from the top portion P1 toward the proximal end side and that are connected to the outer surfaces 15g and the front/back faces 15h, and excision surfaces 15c and 15d, which are formed of inclined surfaces that start from the top portion P1 toward the proximal end side up to substantially the center, are formed. The top portion P2 also has the same configuration as that of the top portion P1 having line symmetry (FIG. 4: V2-V1-V2). With such shapes, valley portions V1 and V2 are formed at the position in which the excision surfaces 15c and 15d of the two of the top portion P1 and the top portion P2 are joined with each other.

FIG. 5 illustrates a cross-sectional shape of a wedge shape of the top portion P1 taken along line A-A' in the axial direction illustrated in FIG. 3 and illustrates a cross-sectional shape of a wedge shape of the valley portion V1 taken along line B-B' in the axial direction illustrated in FIG. 3.

As illustrated in FIG. 5, these valley portions V1 and V2 depict a valley line S2 in which the valley portion V1 is used as the distal end side and that has a wedge shape (projection shape) protruding ahead of the valley portion V2 in the axial direction.

Furthermore, regarding a tip angle $\theta_1$ of the top portion P1 and a tip angle $\theta_2$ of the top portion P2 formed by the edge line R1 and the ridge line S1 at the distal end portion 15f illustrated in FIG. 3 and, furthermore, an angle $\theta_3$ of the wedge of the top portion P1 in the thickness direction and an angle $\theta_4$ of the wedge of the valley portion V1 in the thickness direction illustrated in FIG. 5, a processing speed thereof is increased as the angles are decreased. However, the angles are appropriately set by considering a crushing level of a target part using ultrasound vibrations and considering the depression-projection state of the bottom surface generated at the time of forming a hole having a bottom. Thus, if a treatment target part is excised, the treatment target part is excised by the excision surfaces 15c and 15d, passes over the surface of the base portion 15e on the proximal end side, and is discharged to the rear of the distal end treatment portion 15.

FIG. 6 illustrates a shape of the bottom surface of the hole formed by the distal end portion 15f of the distal end treatment portion 15 illustrated in FIG. 2. The bottom surface shape has the same shape of the depression-projection shape of the distal end portion 15f and the positions associated with the top portions P1 and P2 are the deepest positions.

Figure 7:
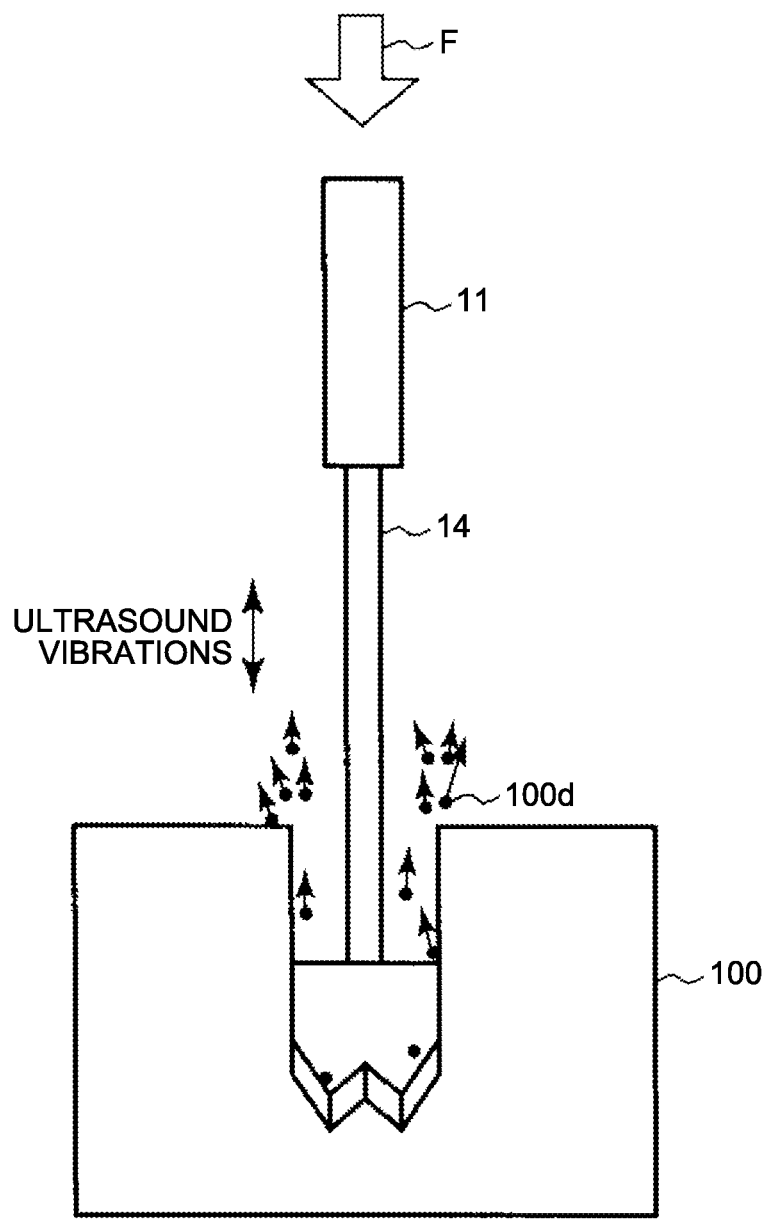
FIG. 7 is a diagram schematically illustrating a state in which a bone hole is formed by the ultrasound device.

In the following, forming a hole performed by the ultrasound probe 14 having the distal end treatment portion 15 according to the embodiment will be described with reference to FIG. 7.

If the distal end treatment portion 15 of the ultrasound probe 14 is pressed against a treatment target part 100 and ultrasound vibrations are applied, the top portions P1 and P2 of the distal end portion 15f come into mechanically collision and crush the treatment target part 100 into fine granularities. Furthermore, by increasing a force F to be applied by an operator, each of the inclined surfaces starting from the top portions P1 and P2 toward the excision surfaces 15a to 15d is inserted such that the treatment target part 100 is pushed therein. At this time, cutting debris (debris) 100d crushed into fine granularities by the top portions P1 and P2 and the excision surfaces 15a to 15d are pressed by the excision surfaces 15a to 15d caused by the pressed force and the vibrations, are pushed aside from the distal end side toward the proximal end side, pass through the distal end treatment portion 15, and are discharged to the rear of the distal end treatment portion 15.

The distal end treatment portion 15 of the probe according to the embodiment is provided with two protruding excision portions (first and second apexes) at the tip of the distal end treatment portion 15. Furthermore, regarding each of the excision portions, a protruding portion formed of a single top portion and inclined surfaces (excision surfaces) that surround the top portion is referred to as the excision portion or an apex. Thus, for example, for a single protruding excision portion, the contact area of the excision surfaces 15a to 15d formed by the inclined surfaces contributing excision (hammering effect) in the direction intersecting the axial direction is increased. Consequently, if a force corresponding to the force F1 at a single excision portion per unit of area is multiplied by each of the two excision portions according to the embodiment, a force F2 (F1<F2) that is about twice as much as the force F1 is applied to the distal end portion 15f and, at the time at which processing is started, a crush of the treatment target part having the same area is simultaneously started at the apex of the tip of each of the plurality of protruding portions and, if a double force is applied, the processing speed can be increased by a factor of two. Namely, at the time at which the processing is started, the force to be applied is increased by a factor of two or three, the processing speed is increased by a factor of two or three compared with a case of using a distal end treatment portion having a single apex. In contrast, if the same processing speed may be used, it is possible to reduce the force to be applied and thus reducing the work load of an operator compared with a case of using a distal end treatment portion having a single excision portion.

Because the distal end treatment portion 15 of the probe according to the embodiment includes two protruding excision portions, there is no need to provide a fluid or a fluid channel for discharging cutting debris. Therefore, the configuration of devices is simplified compared with the device described in which an outlet head for flowing out a fluid is provided toward a center of inclined surface on the inner side. Additionally, the weight of the probe itself is not increased, and the load applied to an operator is not increased.

Furthermore, the hole to be formed is formed by digging down the target portion while maintaining the shape of an opening portion. Furthermore, regarding the hole to be formed, it is possible to form a flat wall surface by being matched with the shape and the size of the hole part without generating an unnecessary gap, which makes it possible to expect enhancement of recovery.

Figure 8:
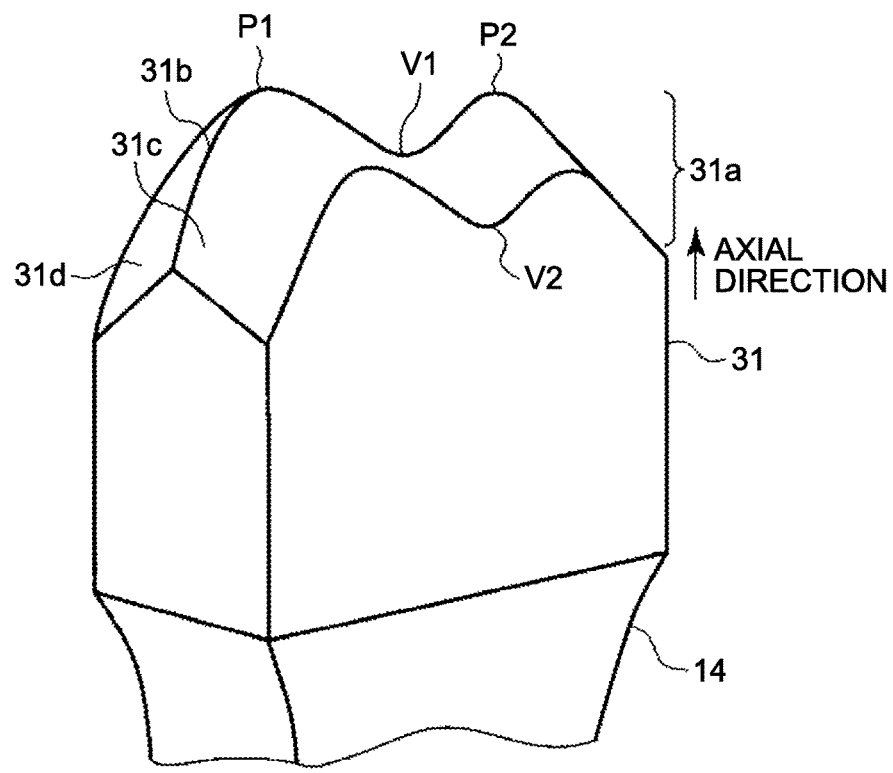
FIG. 8 is a diagram illustrating an appearance shape, viewed from the oblique direction, of a distal end treatment portion of an ultrasound device according to an exemplary embodiment.

Another exemplary embodiment will be described below with reference to FIG. 8. FIG. 8 is a diagram illustrating an appearance shape, viewed from the oblique direction, of a distal end treatment portion of an ultrasound device according to this exemplary embodiment. In the embodiment described above, the configuration is formed such that the edge line R1 is formed by linearly connecting the top portions P1 and P2 to the valley portion V1 of the distal end portion 15f of the distal end treatment portion 15.

In contrast, in this embodiment, a configuration is formed by a curved edge line 31b, which connects the top portions P1 and P2 to the valley portion V1 of an distal end portion 31a of a distal end treatment portion 31 by a curved line, and is formed by excision surfaces 31c and 31d, which are arranged on both sides of the curved edge line 31b. Furthermore, the excision surfaces 31c and 31d are curved in a wavy shape in accordance with the curved edge line 31b; however, in the cross section having the same shape as that taken along line A-A' in the axial direction illustrated in FIG. 3, the linearly wedge shape, i.e., a straight line with a slope, is formed.

According to this embodiment, the same effect as that of the embodiment described above is obtained and, furthermore, because the top portions P1 and P2 of the distal end portion 31a are linearly brought into contact with the treatment target part, when compared with the configuration of a top portion whose distal end is sharp and that is brought into contact with a target portion as a point, it is possible to perform treatment without damaging tissue by the sharp top portion.

Figure 9:
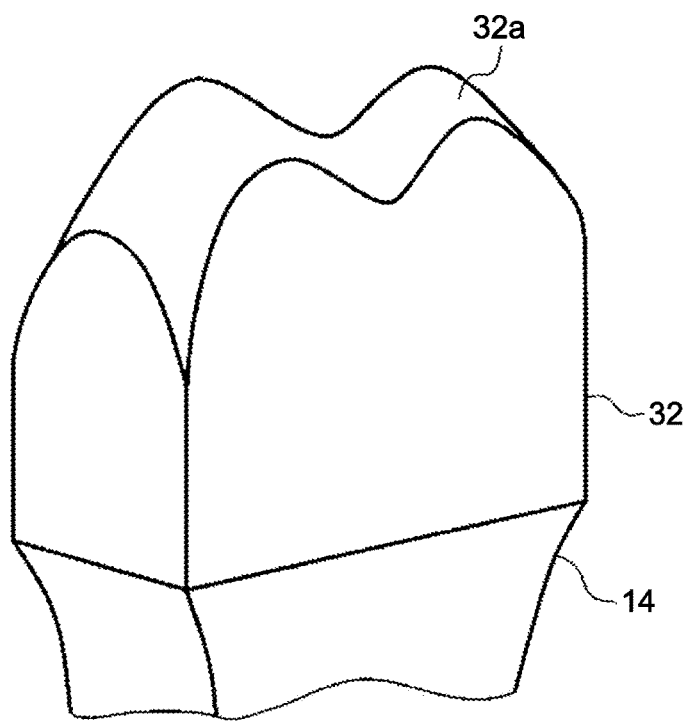
FIG. 9 is a diagram illustrating an appearance shape, viewed from the oblique direction, of a distal end treatment portion of an ultrasound device according to an exemplary embodiment.

Another exemplary embodiment will be described below with reference to FIG. 9. FIG. 9 is a diagram illustrating an appearance shape, viewed from the oblique direction, of a distal end treatment portion of an ultrasound device. In the embodiment described above, the curved edge line 31b is formed and the excision surfaces 31c and 31d are formed by the flat inclined surfaces. In contrast, in this embodiment, in addition to the curved edge line 31b according to the embodiment described above, an excision portion is provided that is formed by a curved surface edge line such that an excision surface 32a is formed by a curved surface instead of the flat inclined surface.

According to this embodiment, the same effect as that of the above embodiment is obtained and, furthermore, because the top portions P1 and P2 of the excision surface 32a are linearly brought into contact with the treatment target part, when compared with the configuration of a top portion whose distal end is sharp and that is brought into contact with a target portion as a point, it is possible to increase the efficiency of insertion and it is thus possible to decrease a risk to other tissue.

Figure 10:
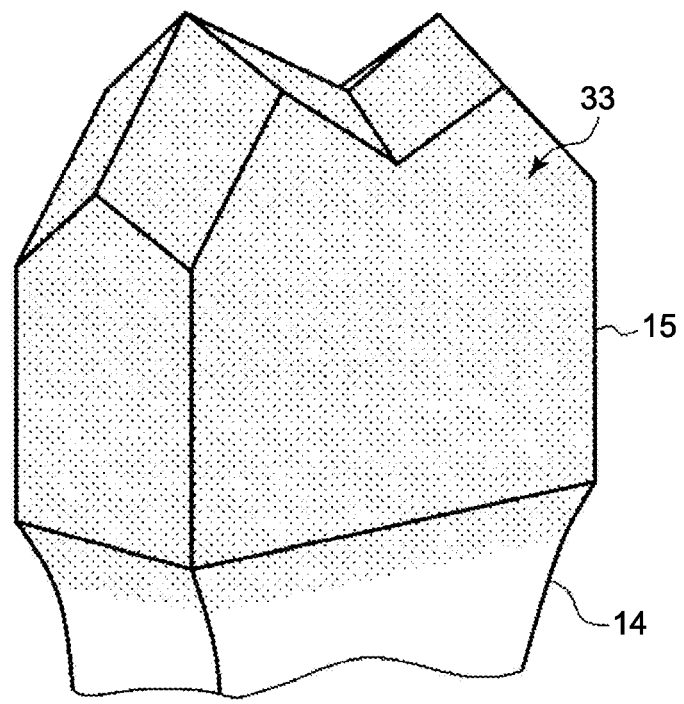
FIG. 10 is a diagram illustrating an appearance shape, viewed from the oblique direction, of a distal end treatment portion of an ultrasound device according to an exemplary embodiment.

Another exemplary embodiment will be described below with reference to FIG. 10. FIG. 10 is a diagram illustrating an appearance shape, viewed from the oblique direction, of a distal end treatment portion of an ultrasound device according to this embodiment. A configuration is formed by performing minute depression-projection processing on the surface of the distal end treatment portion according to the embodiment described above and then a depression-projection surface is formed. As a processing method, for example, mechanical polishing, such as a blasting process, or other surface processes may be used.

According to this embodiment, in addition to the same effect as that of the embodiment described above, because the distal end treatment portion has a minute gap with respect to a processed surface, it is possible to easily move the cutting debris generated in the treatment target part caused by excision toward the rear of the distal end portion, which makes it possible to efficiently perform excision.

Figure 11:
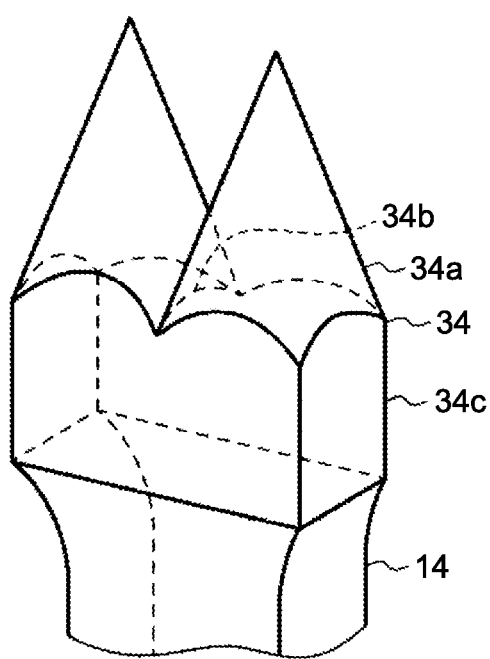
FIG. 11 is a diagram illustrating an appearance shape, viewed from the oblique direction, of a distal end treatment portion of an ultrasound device according to an exemplary embodiment.

Below another exemplary embodiment will be described with reference to FIG. 11. FIG. 11 is a diagram illustrating an appearance shape, viewed from the oblique direction, of a distal end treatment portion of an ultrasound device according to the present embodiment. In this embodiment, the components other than a distal end treatment portion are the same as those in the embodiment described above and descriptions thereof here will be omitted.

A distal end treatment portion 34 of the probe according to the embodiment is provided with two excision portions 34a that protrudes in a conical shape. The position in which the excision portions 34a are brought into contact with each other in a form of a valley line 34b that protrudes in a mountain shape (projection shape) in which the center is higher than both sides. Furthermore, the number of the excision portions 34a is not limited to two and an arbitrary number of the excision portions 34a may also be provided.

According to the embodiment, the cutting debris crushed into fine granularities by the excision surface having the conical surface of an excision portion 34a having the conical shape passes through a base portion 34c from the conical surface and is discharged to the rear of the distal end treatment portion 34. Furthermore, in also the valley portion, because the cutting debris is discharged from the center of the valley line 34b having the mountain shape toward the outer surface, the cutting debris is not retained in the valley portion. Furthermore, because there is no need to prepare a fluid and a fluid channel for discharging the cutting debris, it is possible to simplify the configuration of devices, the weight of the probe itself is not increased, and the load applied to an operator is not increased. Other than these, with the embodiment, it is possible to obtain the same effect as that of the embodiment described above.

Figure 12:
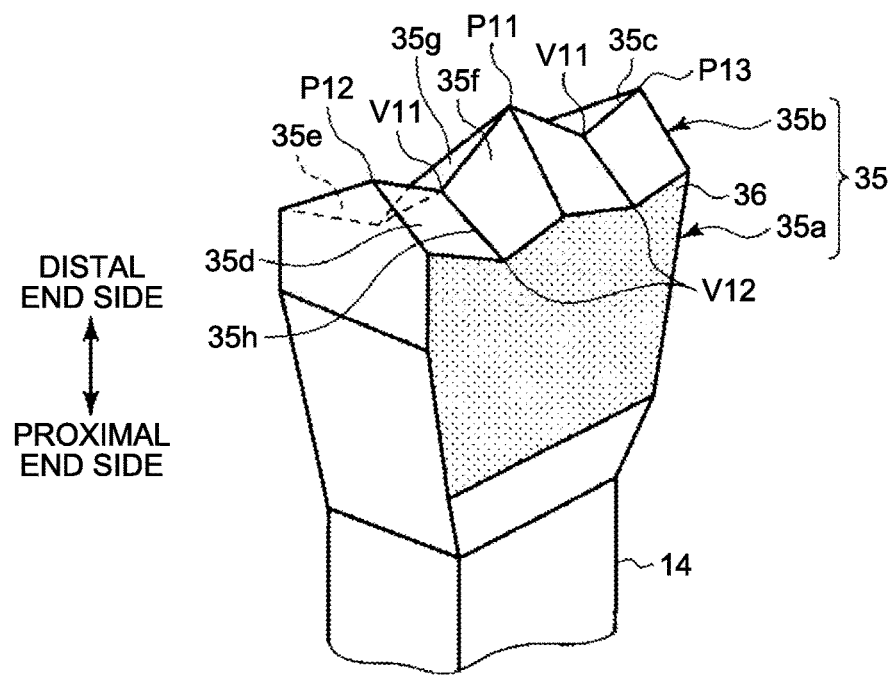
FIG. 12 is a diagram illustrating an appearance shape, viewed from the oblique direction, of a distal end treatment portion of an ultrasound device according to an exemplary embodiment.

Below another exemplary embodiment will be described with reference to FIG. 12. FIG. 12 is a diagram illustrating an appearance shape, viewed from the oblique direction, of a distal end treatment portion of an ultrasound device according to the present embodiment. In this embodiment, the components other than a distal end treatment portion are the same as those in the embodiment described above and descriptions thereof here will be omitted. A distal end treatment portion 35 is an excision tool using ultrasound vibrations and is constituted by a base portion 35a and a distal end portion 35b as illustrated in FIG. 12.

The base portion 35a is gradually increased in cross section toward the distal end side and is the maximum external shape portion that defines a contour shape (or an external shape) of the hole formed by the distal end portion 35b. By forming a cross-sectional shape, such as elliptical shape or a polygonal shape other than the rectangular shape, of the base portion 35a in accordance with a purpose, various kinds of desired holes can be formed.

The distal end portion 35b linearly connects, by using an edge line 35c, three top portions (projecting portions) P11, P12, and P13, which are provided on both sides and at the center thereof, to two valley portions V11 and V12, which are provided between the top portions P11, P12, and P13. On both sides of the edge line 35c, four excision surfaces 35d to 35g, which are formed by inclined surfaces in a section obtained by projecting the outer diameter shape illustrated in FIG. 4 described above, are formed by eight excision surfaces so as to have line symmetrically with respect to the center of the distal end portion 35b. Of course, the shape of the distal end portion 35b is arbitrary; therefore, the number of top portions and the number of excision surfaces are not limited and the number thereof may also be easily and appropriately changed and set. Furthermore, the projected shape is other than a perfect circular shape, such as a shape formed by a drill and is one of the shape enclosed by a straight line, or the shape enclosed by a curved line, or the shape enclosed by a combination of the straight line and the curved line. For example, a polygonal shape, a flower shape, a track shape, and a rounded rectangular shape may be used for the embodiment.

With this shape, similarly to the cross-sectional shape of the valley portion V1 illustrated in FIG. 5 described above, the valley portions V11 and V12 depict valley lines in which the valley portion V11 corresponds to the distal end side and has a shape of the wedge shape (projection shape) protruding ahead of the valley portion V12 in the axial direction. Consequently, the cutting debris generated in a valley line 35h moves to the proximal end side over the valley line 35h.

Furthermore, it may also be possible to perform fine depression-projection processing on the surface of the base portion 35a by using mechanical polishing, such as the blasting process described above, or other surface processes (chemical treatment, such as electrolytic polishing), and form the depressions and a projections surface 36.

According to the embodiment, it is possible to obtain the same effect as that of the embodiment described above. Furthermore, because the number of the valley portions is increased, the generated cutting debris is discharged toward the rear of the base portion 35a (proximal end side) in a distributed manner, thereby it is possible to efficiently discharge the cutting debris from the contact surface between the excision surfaces and the treatment target part.

Figure 13:
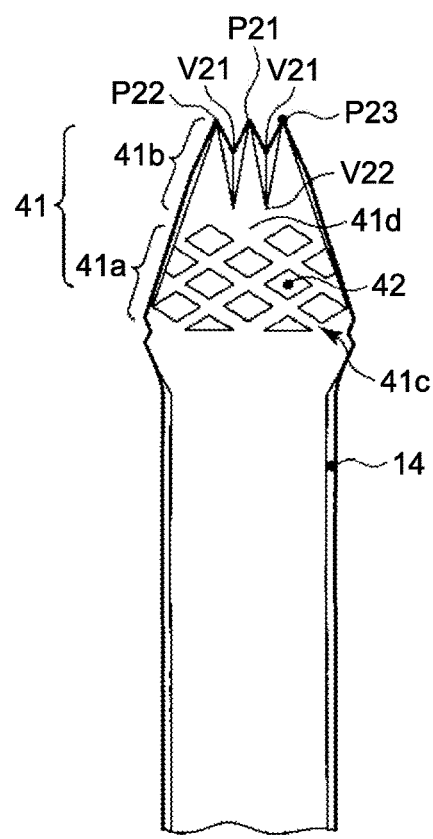
FIG. 13 is a diagram illustrating an appearance shape of a distal end treatment portion of an ultrasound device according to an exemplary embodiment.

Below another exemplary embodiment will be described with reference to FIG. 13. FIG. 13 is a diagram illustrating an appearance shape of a distal end treatment portion of an ultrasound device according to the present embodiment. In this embodiment, the components other than a distal end treatment portion are the same as those in the embodiment described above and descriptions thereof here will be omitted. In the embodiment described above, the side face is in a shape of a vertical surface that is parallel with the axial direction; however, in this embodiment, excision surfaces are formed by also using inclined surfaces for the side face.

A distal end treatment portion 41 according to the present embodiment is an excision tool using ultrasound vibrations and has a substantially quadrangular pyramid shape tapered on the distal end side viewed from the front face and from the side face. Each of the inclined surfaces functions as the excision surface and is formed by a base portion 41a and a distal end portion 41b.

On at least the front face/back face of the base portion 41a, a plurality of diamond shaped convex protrusions 42 functioning as an excision portions are arrayed and formed in a groove 41c that has a mesh pattern. In particular, the generated cutting debris passes through the groove 41c leading to the proximal end side formed by the diamond shaped convex protrusions 42 and is discharged to the proximal end side.

The distal end portion 41b is a flat inclined surface 41d continued from the groove 41c that has a mesh pattern and is provided with, on the distal end, similarly to the embodiment described above with respect to FIG. 12, at least three top portions P21, P22, and P23 and two valley portions V21 that are cut into a V shape between the three top portions P21, P22, and P23. The V-shaped groove of the valley portions V21 are formed in a tapered shape so as to be gradually connected to the flat inclined surface 41d. FIG. 13 illustrates the configuration in which the valley portions V21 are formed on the front face side; however, it may also be possible to form the same valley portions V21 on the side face of the distal end portion 41b.

The distal end treatment portion 41 has a rectangular shape in cross section and is the maximum external shape portion that defines a contour shape (or an external shape) of the hole formed by the proximal end side of the base portion 41a. By forming a cross-sectional shape, such as elliptical shape or a polygonal shape other than the rectangular shape, of the base portion 15e in accordance with a purpose, various kinds of desired holes can be formed. Furthermore, in also the embodiment, it may also be possible to perform fine depression-projection processing on the surface by using mechanical polishing, such as the blasting process described above, or other surface processes.

According to the embodiment, it is possible to obtain the same effect as that of the embodiments described above. Furthermore, because the number of the distal end portions and the valley portions is increased, the generated cutting debris is discharged toward the rear of the base portion 35a (proximal end side) in a distributed manner, thereby it is possible to efficiently discharge the cutting debris from the contact surface between the excision surface and the treatment target part.

Because the distal end treatment portion 41 according to the present embodiment is shaped as a substantially quadrangular pyramid tapered on the distal end side, each of the inclined surfaces functions as the excision surface and it is thus possible to further increase a processing speed compared with the other embodiments.

Furthermore, the base portion 15e according to the distal end treatment portion 15 described above is the maximum external shape portion corresponding to the size of the hole in which a projected shape is formed when viewed from the distal end side of the treatment portion (cutting portion) and is configured such that, based on the maximum external shape portion thereof, the proximal end side is shaped as a tapered narrow part.

From the viewpoint of friction and discharging the cutting debris from the rear side, it is preferable that the length of the axial direction of the maximum external shape portion be short. However, if the length thereof is insufficient, the intensity of the probe may possibly be decreased and, furthermore, a length is accordingly needed to make a straight hole. The length of the axial direction of the base portion 15e is set by taking into consideration of these points.

Thus, as illustrated in FIG. 13, the groove 41c having a mesh pattern is formed on at least the front face/back face of the base portion 41a having the maximum shape by arraying the plurality of the diamond shaped convex protrusions 42 functioning as the excision portions. The generated cutting debris passes through the groove 41c leading to the proximal end side formed by the diamond shaped convex protrusions 42 and is discharged to the proximal end side. The grove leading to this type of proximal end side can be used for the base portion of the distal end treatment portion according to any of the other exemplary embodiments described above with respect to FIGS. 2-12, for example.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound device comprising:
   an ultrasound generator configured to generate ultrasound vibrations; and
   an ultrasound probe that is acoustically connected, on a proximal end side, to the ultrasound generator, and is configured to transmit the ultrasound vibrations, the ultrasound probe including, on a distal end side, a distal end treatment portion including:
      a base portion disposed on a proximal end side of the distal end treatment portion, the distal end treatment portion being configured to form a bone hole having a cross-sectional shape identical to that of the base portion, and
      a distal end portion disposed on a distal side of the base portion, the distal end portion including a plurality of projections arranged in a row, each projection being formed of at least one excision surface that is inclined from a base of the projection to a distal top of the projection, the at least one excision surface being configured to finely crush the bone, wherein:
      adjacent projections are adjoined to one another by a valley formed therebetween, and the valley includes a valley peak at a distal-most meeting point of the adjacent projections such that a surface of the valley extending distally from a point at which the valley meets an outer surface of the base portion to the valley peak is inclined;
      wherein the plurality of projections protrude in a direction of a longitudinal axis of the distal end treatment portion.

2. The ultrasound device according to claim 1, wherein a cross-sectional area of the base portion of the distal end treatment portion is greater than a cross-sectional area of a probe main body portion connected to the proximal end side of the distal end treatment portion.

3. The ultrasound device according to claim 1, wherein the distal end treatment portion comprises a flat outer surface, a curved outer surface, or a combination of a flat outer surface and a curved outer surface.

4. The ultrasound device according to claim 1, wherein a surface of the distal end treatment portion includes irregularities formed by a blasting process or a mechanical polishing process.

5. The ultrasound device according to claim 1, wherein the valley peak is disposed at a central point between the adjacent projections.

6. The ultrasound device according to claim 2, wherein a proximal end side the base portion is tapered in a direction toward the probe main body portion.

7. The ultrasound device according to claim 1, wherein a shape of the distal end treatment portion is not a perfect circular shape.

8. The ultrasound device according to claim 1, wherein the distal end treatment portion does not comprise a fluid channel for discharging cutting debris.

9. The ultrasound device according to claim 1, wherein the excision surface of at least one projection is curved.

10. The ultrasound device according to claim 9, wherein each excision surface is curved.

11. The ultrasound device according to claim 1, wherein each projection comprises:
    an edge line extending proximally from the top of the projection to the valley peak to connect the top of the projection to the valley, and
    a ridge line extending proximally from the top of the projection to an outer surface of the base portion.

12. The ultrasound device according to claim 11, wherein each projection comprises:
    a plurality of excision surfaces that extend from the edge line and the ridge line in a direction orthogonal to the edge line and the ridge line toward a proximal end side and toward an outer surface of the base portion.

13. The ultrasound device according to claim 12, wherein the plurality of excision surfaces are flat surfaces.

14. The ultrasound device according to claim 13, wherein the valley is formed at a position in which two excision surfaces of one projection are joined with two excision surfaces of a second adjacent projection.

15. The ultrasound device according to claim 1, wherein the base portion comprises a plurality of convex protrusions arranged in a groove having a mesh pattern.

16. The ultrasound device according to claim 1, wherein each projection has a conical shape.

17. The ultrasound device according to claim 1, wherein an outer surface of the distal end treatment portion is tapered in a direction from a proximal end to a distal end.

18. The ultrasound device according to claim 1, wherein the distal end treatment portion includes two projections.

19. The ultrasound device according to claim 1, wherein the distal end treatment portion includes three projections.

* * * * *